United States Patent [19]

Morrison et al.

[11] Patent Number: 4,748,986

[45] Date of Patent: Jun. 7, 1988

[54] FLOPPY GUIDE WIRE WITH OPAQUE TIP

[75] Inventors: David W. Morrison, San Jose; Wilfred J. Samson, Saratoga, both of Calif.

[73] Assignee: Advanced Cardiovascular Systems, Inc., Mountain View, Calif.

[21] Appl. No.: 9,092

[22] Filed: Jan. 29, 1987

Related U.S. Application Data

[63] Continuation of Ser. No. 802,599, Nov. 26, 1985, abandoned, which is a continuation-in-part of Ser. No. 560,802, Dec. 12, 1983, abandoned.

[51] Int. Cl.⁴ .................... A61M 10/00; A61M 25/00
[52] U.S. Cl. ................................. 128/772; 128/657; 604/170
[58] Field of Search ............... 128/772, 657; 604/170, 604/281, 282

[56] References Cited

U.S. PATENT DOCUMENTS

| | | | |
|---|---|---|---|
| 3,521,620 | 7/1970 | Cook | 128/772 |
| 4,003,369 | 1/1977 | Heilman et al. | 128/772 |
| 4,538,622 | 9/1985 | Samson et al. | 128/772 |
| 4,548,206 | 10/1985 | Osborne | 128/772 |
| 4,554,929 | 11/1985 | Samson et al. | 128/772 |

Primary Examiner—Stephen C. Pellegrino
Attorney, Agent, or Firm—Fulwider, Patton, Rieber, Lee & Utecht

[57] ABSTRACT

Floppy guide wire comprising an elongate flexible element formed of a metallic material. The element has a cylindrical proximal portion, a tapered intermediate portion and a flattened distal portion. A coil formed of a substantially radiopaque material is secured to said element and is generally concentric with the element. The coil extends beyond a rounded metallic protrusion is carried by the distal extremity of the coil and is spaced from the distal extremity of the flexible elongate element. A safety wire is disposed within the coil and is secured to the protrusion and to the flexible elongate element.

13 Claims, 2 Drawing Sheets

U.S. Patent   Jun. 7, 1988   Sheet 1 of 2   4,748,986
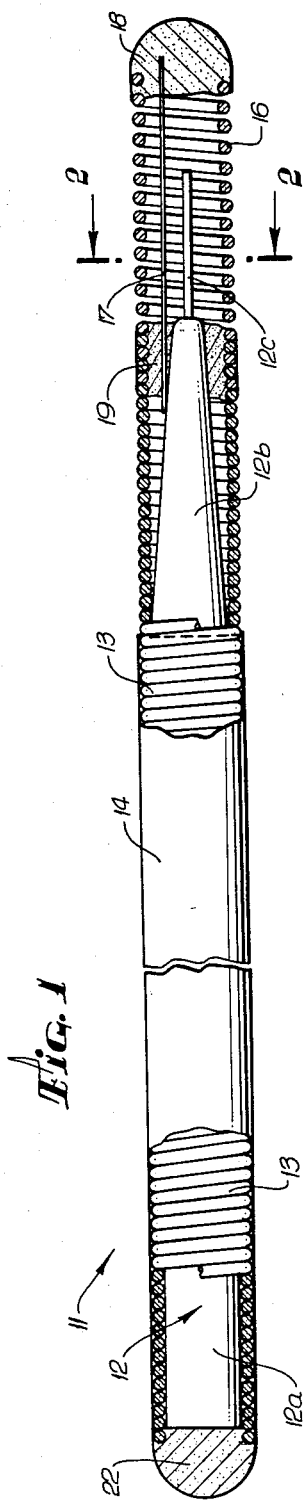
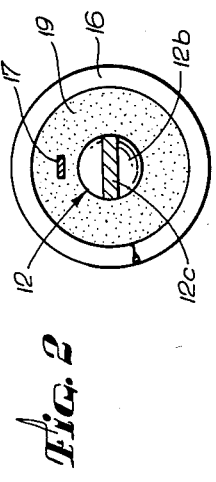
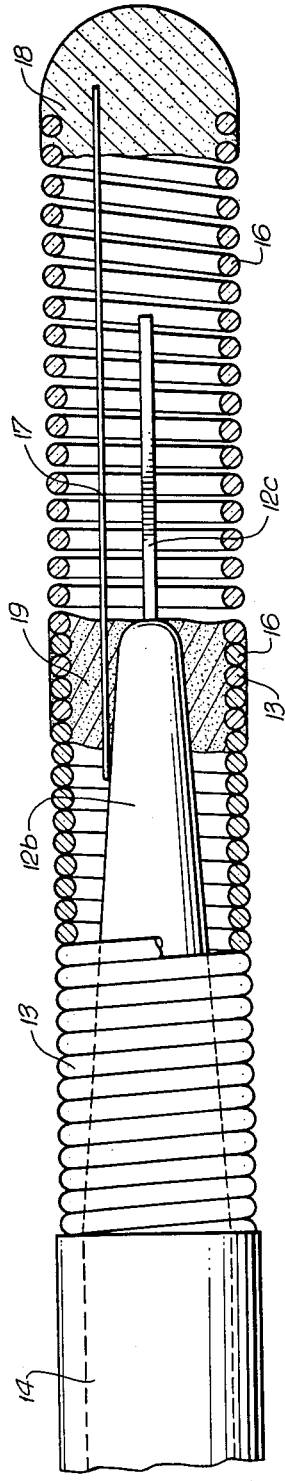

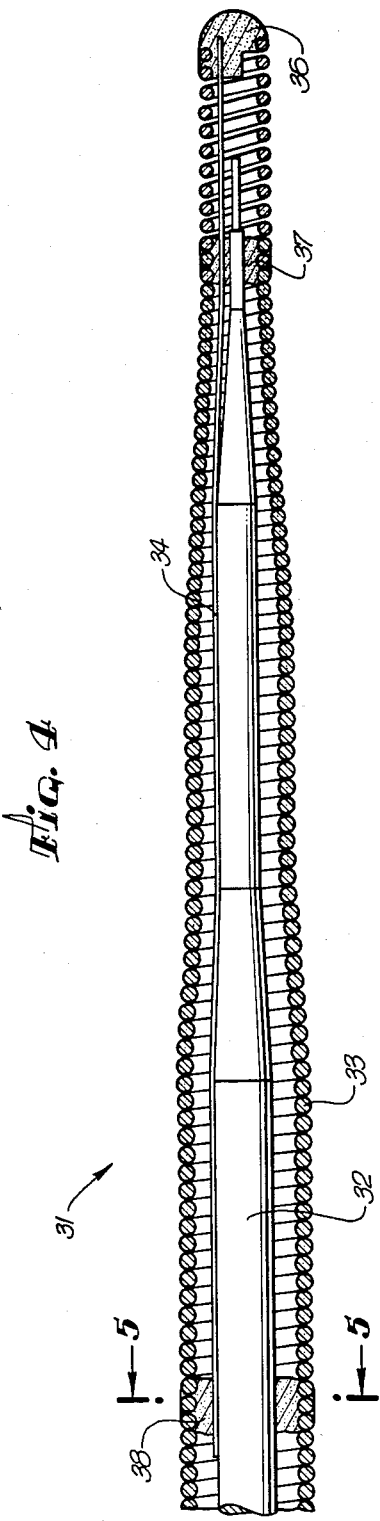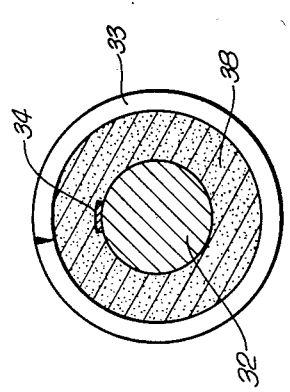

FLOPPY GUIDE WIRE WITH OPAQUE TIP

This is a continuation of application Ser. No. 802,599, filed 11-26-85, now abandoned, which is a continuation-in-part of Ser. No. 560,802, filed 12-12-83, now abandoned.

This invention relates to floppy guide wires for use in introducing catheters into vascular systems and more particularly into cardiovascular systems in humans and which is provided with an opaque tip.

Guide wires have heretofore been provided to facilitate the insertion of catheters into cardiovascular systems. One such guide wire is disclosed in application Ser. No. 513,222, filed on July 13, 1983. In connection with such guide wires it has been found that it is difficult to introduce such guide wires into very small vessels and particularly into partially occluded segments of such vessels. There is therefore a need for an improved guide wire which can be successfully introduced into the small vessels in vascular systems and more particularly to provide one which is very flexible or floppy to facilitate travel in the vessel and in particular a vessel which is highly tortuous.

In general, it is an object of the invention to provide a floppy guide wire for catheters which can be introduced into small vessels in vascular systems and particularly in cardiovascular systems in humans.

Another object of the invention is to provide a floppy guide wire of the above character which has torque capabilities.

Another object of the invention is to provide a floppy guide wire of the above character which has a very flexible distal end.

Another object of the invention is to provide a floppy guide wire of the above character in which the very flexible distal end has a greater freedom of movement of direction in one plane than in other directions.

Another object of the invention is to proivde a floppy guide wire of the above character which will not elongate and/or fracture.

Additional objects and features of the invention will appear from the following description in which the preferred embodiment is set forth in detail in conjunction with the accompanying drawings.

FIG. 1 is a side elevational view partially in cross section of a floppy guide wire incorporating the present invention.

FIG. 2 is a cross sectional view taken along the line 2—2 of FIG. 1.

FIG. 3 is an enlarged view of the distal portion of the floppy guide wire shown in FIG. 1.

FIG. 4 is an enlarged side elevational view partially in cross section of the distal extremity of another embodiment of a floppy guide wire incorporating the present invention.

FIG. 5 is an enlarged cross sectional view taken along the line 5—5 of FIG. 4.

The floppy guide wire of the present invention for use in inserting catheters consists of an elongate element formed of a metallic material having torsional capabilities. The element is provided with a cylindrical proximal portion, a tapered intermediate portion and a flattened distal end portion. A coil formed of a substantially radiopaque material is secured to the element so that it is concentric with the element and extends beyond the distal extremity of the element. A rounded protrusion is carried by the distal extremity of the coil. A safety wire is disposed within the coil and is secured to the protrusion and at one or more locations to the flexible elongate element.

More particularly as shown in FIGS. 1, 2 and 3, the floppy guide wire 11 consists of a flexible elongate element 12 formed of a suitable metallic material having a high torsional strength such as stainless steel. Other materials can be utilized such as certain carbon steels as well as titanium and beryllium copper. The flexible elongate element 12 can be in the from of a wire-like hollow cylindrical element or in the form of a wire-like cylindrical core. One particular material utilized for the flexible elongate element 12 has been No. 304 stainless steel which includes approximately 20% chromium and 10% nickel and has a minimum of 240 psi tensile strength. The material is preferably work-hardened by drawing 0.150 inch stainless steel wire down to wire having a diameter of 0.010 inches. The wire after being work-hardened is straightened and cut to the desired length. Thereafter, it is then centerless ground and the tip flattened to provide the conformation shown in FIG. 1.

The guide wire 11 has a suitable length which depends upon the application for which it is used. As a typical guide wire it can have a length of approximately 175 centimeters plus or minus 5 centimeters. The flexible elongate element 12 has a total length of slightly less than the 175 centimeters as, for example, a length of approximately 173.5 centimeters for a purpose hereinafter described. The flexible elongate element 12 is provided with an elongate generally cylindrical proximal portion 12a which extends almost the entire length of the floppy guide wire 11. It is adjoined by an intermediate tapered portion 12b which in turn is adjoined by a distal flattened portion 12c. If desired, a cylindrical portion having a diameter of 0.002 inches could be substituted for the flattened portion. Thus it can be seen that the portions 12b and 12c form the distal portion of the flexible elongate element 12. The cylindrical portion 12a has suitable dimensions such as a diameter ranging from 0.005 to 0.012 inches and preferably a diameter of approximately 0.010 inches. The tapered portion 12b tapers down from a larger diameter to a smaller diameter as, for example, down to 0.003 and 0.004 of an inch. The tapered portion can have a suitable length as, for example, four centimeters plus or minus 2 centimeters. The flattened portion 12c can have a suitable length such as 5.5 centimeters plus or minus 2 centimeters. The flattened portion typically can be formed by centerless grinding portion to a uniform dimension of 0.003 to 0.004 inches in diameter, after which this portion is stamped or rolled flat. When so flattened, the portion 12c can have a length of approximately 1.5 centimeters plus or minus 1 centimeter. It also can be characterized as having a thickness of approximately 0.002 and a width from 0.002 to 0.008 depending upon the diameter of the starting wire. When the distal extremity of the flexible elongate element has been flattened in this manner, it can be seen that this distal portion will have much greater flexibility of movement in a direction in a plane which is perpendicular to the width of the flattened portion than in other directions and in particular, parallel to the lane of the flattened portion.

An elongate coil 13 formed of a suitable material such as stainless steel is coaxially disposed on the flexible elongate element 12 and extends substantially the entire length thereof from the proximal end to near the commencement of the tapered portion 12b. The coil 13 can be formed of wire having a diameter from 0.001 to 0.005 and preferably a diameter of 0.003 inches. With such dimensions the coil would have an outer diameter ranging from 0.007 inches to 0.025 inches. The coil 13 is tightly wound so that the turns are bottomed out or butt each other. In order to provide a smooth relatively slippery or unctuous surface, a coating 14 of a suitable material such as Teflon is provided on the coil 13 to generally provide for lubricity when exposed to blood and contrast agents which are notably sticky.

Another elongate coil 16 is provided which adjoins the coil 13. The coil 16 is formed of material which is substantially opaque to x-rays. For that reason it should be formed of a material which has a density of at least 13 grams/cm$^3$. Suitable materials meeting this requirement include gold, tantalum, tungsten, platinum, iridium, rhenium and alloys of these materials. One coil 16 formed of this material was formed from a platinum alloy wire having dimensions substantially the same as the dimensions of the wire utilized for forming the coil 13. The proximal portion of the coil 16 was formed with turns which are bottomed out on each other. However, near the distal end of the coil 13, the turns are stretched or spaced apart a suitable distance as, for example, 0.003 inches plus or minus 0.003 inches. This spacing in the platinum coil provides additional flexibility in the distal extremity of the platinum coil. The distal extremity of the coil 13 and the proximal extremely of the coil 16 can be threaded together as shown particularly in FIGS. 2 and 3 so that a connection is formed therebetween. Alternatively, if desired, the two coils 13 and 16 can have these same ends butted together.

A safety ribbon 17 formed of a suitable material such as tungsten is provided and is disposed internally of the coil 13. It can have suitable dimensions such as a thickness of 0.001 inches and a width of 0.003 inches. A metallic rounded protrusion 18 in the form of a gold alloy slug 18 is disposed in the distal extremity of the coil 16. Typically, this is formed by brazing a small slug 18 into the distal extremity of the coil. As can be seen, the safety ribbon 17 is brazed into the slug 18 and extends rearwardly from the protrusion or slug 18 into a region where it overlies the flexible elongate element 12 as, for example, the tapered portion 12b of the element 12. The distal extremity of the coil 13, the proximal extremity of the coil 16 and the proximal extremity of the safety ribbon 17 and the tapered portion of the element 12 are bonded into a unitary assembly by a brazing compound 19.

A rounded protrusion 22 formed of a suitable material such as a gold coil-like preform 22 is secured to the proximal extremity of the coil 13 by suitable means such as brazing.

From the construction herein described, it can be seen that the guide wire 11 has a substantially continuous diameter throughout its entire length. The transition point between the stainless steel coil 13 and the platinum coil 16 can only be denoted by the brazing 19. The brazing 19 is applied in such a manner that a smooth surface is provided by the outer surface of the brazing so that a substantially smooth, relatively slippery exterior surface is provided by the guide wire 11.

The guide wire 11 hereinbefore described can be utilized as a guide wire for inserting catheters in vascular systems and particularly into cardiovascular systems. The entire guide wire is relatively floppy and can be readily introduced in a manner well known to those skilled in the art. The distal extremity of the guide wire is very flexible. The flexibility is enhanced because the distal extremity of the coil 16 is spaced from the portion 12c of the flexible element 12. The tungsten safety ribbon 17 is addition to providing a safety ribbon which prevents extension of the coil 13 when it is being retracted and from becoming separated from the flexible elongate element 12, also provides means which can be shaped by hand so as to provide a predetermined conformation to the distal extremity of the coil 16. Thus in addition to being very flexible, the distal extremity of the guide wire 11 can be preformed. The flattened portion 12c of the element 12 provides extreme flexibility in one direction, namely, in a direction perpendicular to the plane of the flattened portion 12c while at the same time providing some rigidity in other directions to facilitate negotiation of difficult regions in the vascular system. Since the distal extremity of the guide wire 11 is relatively light, it floats in a moving blood stream as, for example, one encountered in the human cardiovascular system which facilitates movement of the guide wire through the vessels of the vascular system.

The construction of the guide wire is relatively simple and is one which can be repeatably manufactured with consistency.

Another embodiment of a floppy guide wire incorporating the present invention is shown in FIGS. 4 and 5 in which the floppy guide wire 31 consists of a flexible elongate element 32 and a flexible tapered coil 33. The flexible elongate element 32 can be formed in the same manner as the flexible elongate element 12 shown in the embodiment in FIGS. 1, 2 and 3. Alternatively, as shown in FIGS. 4 and 5 it can be formed in the manner described in co-pending application Ser. No. 724,624 filed on Apr. 18, 1985 in which the flexible elongate element has a decreasing cross sectional area in a direction towards the distal end. Similarly, the flexible coil 33 can be formed as the flexible coil 13 shown in the embodiment in FIGS. 1, 2 and 3 or preferably, as shown in the FIGS. 4 and 5, it can be formed with a tapered coil of the type described in co-pending application Ser. No. 724,624 filed on Apr. 18, 1985. As described in said co-pending application, the flexible or attenuated tapered coil 33 because it has been centerless ground has had many stresses placed on the same. Therefore to ensure that the distal extremity of the flexible tapered coil 33 and/or the distal extremity of the flexible elongate element 32 will not fracture and break off while it is in use, a safety ribbon 34 is provided. The safety ribbon 34 can be similar to the safety ribbon 17 in FIGS. 1, 2 and 3 and can have a suitable dimension such as a thickness of 0.001 inches and a width of 0.003 inches. The ribbon can be formed of a suitable material such as tungsten which has good tensile strength. The safety ribbon 34 is brazed onto a slug 36 which is formed on the distal extremity of the coil 33.

A portion of the ribbon 34 is also bonded to the flexible elongate 32 in a region adjacent the distal extremity of the same by a brazing compound to form a brazed joint 37 so as to form the distal extremity of the flexible elongate element 32 and a portion of the tapered coil 33 adjacent the distal extremity of the same into a unitary assembly. The safety ribbon 34 also extends from the brazed joint 37 towards the proximal extremity of the floppy guide wire 31 and is secured to an intermediate portion of the flexible elongate element 32 in a region in which the flexible elongate element 32 has a maximum diameter by a brazed joint 38. The safety ribbon 34 can have a suitable length such as 18 centimeters.

Use of the floppy guide wire 31 may now be briefly described. The floppy guide wire 31 is used in the manner hereinbefore described. The distal extremity of the guide wire can be shaped to hold a predetermined configuration. This is made possible because of the planar configuration of the safety ribbon in which it has a dimension in one direction which is substantially greater than the dimension in the opposite direction as, for example, the three-to-one ratio hereinbefore described. This shaping can be accomplished by running the distal extremity of the guide wire between two fingers of the hand to cause it to be formed in a predetermined shape in which the curvature is along a line which corresponds to the plane of the surface of the width of the safety ribbon. The retention of this shape is also aided by the fact that the distal extremity of the flexible elongate element 32 is relatively flat and in which the surface of the flexible elongate element 32 lies in the plane of the surface width of the safety ribbon.

Since the safety ribbon 34 has been formed of a tungsten, it has relatively great strength in tension. Thus, even if the distal extremity of the flexible tapered coil 33 should happen to break off, it will be retained integral with the flexible floppy guide wire 31 so that it can be withdrawn with the guide wire and will not travel into the blood stream of the patient. It can be seen that this is also true if the distal extremity of the flexible elongate element 32 should break off because since the flexible ribbon 34 extends to a major dimension of the flexible elongate element 32 it also will prevent the distal extremity from breaking off and passing into the bloodstream of the patient. Thus it can be seen if the flexible tapered coil 33 and/or the flexible elongate element 32 near the distal extremity of the floppy guide wire should fracture and break off, they will be retained by the safety ribbon 34 so that the broken off part or parts can be retraced with the floppy guide wire without any danger of leaving any portion of the guide wire in the blood vessel of the patient.

The tip 36 is typically formed of gold. A brazing alloy is used rather than solder because the brazing alloy will wet to the tungsten safety ribbon 34 whereas the solder will not. Gold can be utilized for the tip 36 if desired and the safety ribbon 37 can be brazed to the gold.

In summary, the guide wire is floatable in the blood stream. The tips can be preformed by the doctors or radiologists so as to be able to enter different areas of the cardiovascular system. The guide wire is still stiff enough so it can be used as a guide and still floppy enough so that it will not penetrate the wall of the vessel. The guide wire is sufficiently small that it can penetrate lesions and still permit bood flow through an occluded vessel. The tip of the guide wire is substantially radiopaque so that its travel can be observed under conventional fluoroscopy. By way of example, in the event that the guide wire reaches a dead end, a shepherd's hook will be formed in the end of the guide wire which can be observed on the fluoroscope. Because of the ability of the distal extremity of the guide wire to float, it can find and pass through eccentric openings in the vessels.

It can be seen that the guide wires are constructed in such a manner so that they can readily undergo torsional stresses to permit rotation of the distal extremity of the guide wire to facilitate guiding the guide wire into the blood vessel. In the event the distal extremity of the guide wire should accidentally break off because of torsional stresses, the piece or pieces which break off will be retained by the safety ribbon because the safety ribbon is brazed to the elongate element in two spaced apart locations so the piece or pieces can be retracted from the blood vessel without danger of a piece of the guide wire becoming separated and passing into the patient's blood stream.

What is claimed is:

1. A floppy guide wire comprising:
   a flexible elongate element formed of a metallic material portion, at least one tapered intermediate portion and a flattened distal portion having the distal extremity thereof unsecured;
   a coil generally concentric with the flexible elongate element formed of a metallic material extending over at least a substantial portion of the proximal portion, the tapered portion, the flattened distal portion, and beyond the unsecured extremity of the distal portion, said coil being secured to said elongate element at an intermediate point along the length thereof and having a rounded metallic protrusion carried by the distal extremity of the coil; and
   a safety wire disposed within the coil which is secured at the distal extremity thereof to the protrusion and at least one location along the length thereof to the flexible elongate element proximally spaced from the flattened distal portion thereof and distally spaced from the proximal extremity of the coil.

2. A guide wire as in claim 1 wherein said coil includes a proximal coil section and a distal coil section having juxtaposed overlapping ends and means joining together the overlapping ends of the coil sections.

3. A guide wire as in claim 2 wherein said distal coil section is formed of radiopaque material.

4. A guide wire as in claim 3 wherein the distal coil section is formed of a platinum alloy.

5. A guide wire as in claim 2 wherein turns of the distal coil section are spaced apart a greater distance than the turns on the proximal portion of the coil to provide additional flexibility in the distal extremity of the guide wire.

6. A guide wire as in claim 1 wherein said overlapping ends are threaded together and wherein the means joining the overlapping ends is a brazing compound.

7. A guide wire as in claim 1 wherein said safety ribbon is formed of a pliable metallic material, said safety ribbon being capable of being shaped so as to provide a curvilinear shape in the distal extremity of the guide wire so that the distal extremity of the guide wire has a curvature along a line which corresponds to the plane of the surface of the width of the safety ribbon, said curvilinear shape being retained solely by the bending of the safety ribbon.

8. A guide wire as in claim 1 wherein said safety wire is secured to the flexible elongate element in at least two spaced apart locations.

9. A guide wire as in claim 8 wherein said safety wire has a proximal extremity which is secured to the flexible elongate element in a region in which the flexible elongate element has its maximum cross sectional area.

10. A guidewire as in claim wherein said safety wire has a length substantially less than the length of the flexible elongate element.

11. A guide wire as in claim 10 wherein said coil is bonded to said flexible elongate element at two spaced apart locations adjacent the distal extremity of the flexible elongate element.

12. A guide wire as in claim 10 wherein the safety wire is bonded to said flexible elongate element at two spaced apart locations.

13. A guide wire as in claim 10 wherein the coil is formed as a tapered coil.

* * * * *

UNITED STATES PATENT AND TRADEMARK OFFICE
CERTIFICATE OF CORRECTION

PATENT NO. : 4,748,986

DATED : June 7, 1988

INVENTOR(S) : David W. Morrison and Wilfred J. Samson

It is certified that error appears in the above-identified patent and that said Letters Patent is hereby corrected as shown below:

Column 1, line 37, delete "of" (first occurrence) and insert therefor --or--.

Column 1, line 39, delete "proivde" and insert therefor --provide--.

Column 2, line 10, delete "from" and insert therefor --form--.

Column 2, line 63, delete "lane" and insert therefor --plane--.

Column 3, line 25, delete "0.003" and insert therefor --0.0003--.

Column 3, line 28, delete "extremely" and insert therefor --extremity--.

Column 4, line 4, delete "is" and insert therefor --in--.

Column 5, line 18, after "ribbon" insert --34--.

Column 5, line 36, delete "retraced" and insert therefor --retracted--.

Column 6, line 7, before "portion" insert --having a cylindrical proximal--.

Column 6, line 57, after "claim" insert --1--.

Signed and Sealed this

Twenty-seventh Day of March, 1990

Attest:

JEFFREY M. SAMUELS

Attesting Officer

Acting Commissioner of Patents and Trademarks